United States Patent [19]

Sievertsson et al.

[11] 4,058,512
[45] Nov. 15, 1977

[54] SYNTHETIC PEPTIDES HAVING GROWTH PROMOTING ACTIVITY

[75] Inventors: Hans Sievertsson, Sollentuna; Ronny Hugo Loritz Lundin, Stockholm; Gertrud Elisabeth Westin Sjodahl, Sodertalje, all of Sweden

[73] Assignee: AB Kabi, Stockholm, Sweden

[21] Appl. No.: 571,995

[22] Filed: Apr. 28, 1975

[51] Int. Cl.² .................... C07C 103/52; A61K 37/00; C12B 9/00

[52] U.S. Cl. ............................. 260/112.5 R; 195/1.7; 424/177

[58] Field of Search .................. 260/112.5 R, 112.5 S, 260/112.5 T

[56] References Cited

U.S. PATENT DOCUMENTS 3,798,203   3/1974   Brugger et al. ............... 260/112.5 T
3,849,388   11/1974  Rittel et al. .................. 260/112.5 T Primary Examiner—Delbert R. Phillips
Attorney, Agent, or Firm—A. A. Orlinger

[57] ABSTRACT

Novel synthetic peptides of the general formula

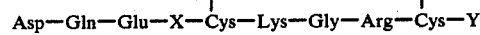

Asp—Gln—Glu—X—Cys—Lys—Gly—Arg—Cys—Y and the corresponding reduced, linear form. The cyclic form of the peptide is produced by oxidation of the corresponding linear compound thereby providing the divalent dithio group —S—S— joining the beta carbon of each of the cysteine moieties. In the above formula X is serine (SER) or lysine (Lys), and Y is OH or Thr-Glu-Gly-Phe. The obtained synthetic peptides, in either form, are useful in promoting growth of cells of mammalian tissues.

7 Claims, No Drawings

SYNTHETIC PEPTIDES HAVING GROWTH PROMOTING ACTIVITY

This invention is that of synthetic peptides of the general formula

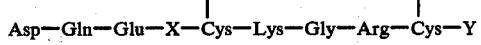

and the corresponding reduced, linear form synthesized from the amino acids: aspartic acid (Asp), glutamine (Gln), glutamic acid (Glu), serine (Ser), glycine (Gly), arginine (Arg), cysteine (Cys), lysine (Lys), threonine (Thr) and phenylalanine (Phe), in each of their two available forms wherein the cysteine residues or moieties in the positions 5 and 9 are a. in a reduced state providing the peptides in their linear forms aspartyl-glutaminyl-glutamyl-X-cysteinyl-lysyl-glycyl-arginyl- cysteinyl-Y, and b. in their oxidized state providing the peptides in their cyclic form having the divalent dithio group —S—S—, joining the beta carbon of each of the cysteine moieties, wherein the link between the two cysteine moieties as customarily represents the dithio group —S—S—. X is serine (Ser) or lysine (Lys), and Y is OH or Thr-Glu-Gly-Phe.

The synthetic peptides are useful in promoting growth of cells of mammalian, for example, human tissue origin. The peptides of the invention also can be used to enhance the production of medically important substances such as vaccines, interferons, etc., for example, in their in vitro production in tissue cell cultivation.

The peptides, in either their linear or cyclic form, can be prepared by utilizing readily available and/or readily producible starting materials. Basic starting materials which can be used in synthesizing the peptides are the earlier above named amino acids. Each of these ten amino acids can be used in its respective appropriately blocked or protected form suitable for use in solid-phase peptide synthesis.

For example, the tertiary-butyloxycarbonyl group can be used to block the amino group of the carboxyl terminal amino acid of the peptide thereby to provide tertiary-butyloxycarbonylphenylalanine (Boc-Phe) or tertiary-butyloxycarbonyl-S-para-methoxybenzylcystein (Boc-Cys (MeOBzl)). The Boc amino acid can be linked to a chloromethylated resin or polypeptide carrier or support resin or other such resin or carrier adapted to have an amino acid removably linked to it. The initial support resin to use may also be a peptide-resin suitable for use in linking up the remaining amino acid one amino acid at a time or by multiples of one amino acid in a sequential operation ultimately to yield the desired protected peptide. The obtained peptide bound to a resin or other carrier then is cleaved or split off by treatment with a compatible suitable acid to give the free peptide unprotected or otherwise protected and thereafter appropriately converted into its unprotected form.

Alternatively the peptides of this invention can be synthesized in solution, using a stepwise approach wherein the selected respective appropriate protected amino acid moieties are added one by one starting, for example, with the phenylalanine moiety at the carboxyl terminal or with the aspartic acid moiety at the amino terminal. The remaining amino acids thereafter are added in the required sequence to provide their specific sequence in the end product peptide.

Alternatively, the tridecapeptides of the invention can be provided by combining various respectively selected polypeptide fragments, for instance, a suitable undecapeptide can be combined with a suitable dipeptide, or a decapeptide can be combined with a compatible tripeptide, a nonapeptide with a tetrapeptide, an octapeptide with a pentapeptide, or a heptapeptide with a hexapeptide. These various smaller polypeptide fragments can be used either in their unprotected or appropriately protected forms.

Alternatively, the nonapeptide of the invention can be provided by combining various respectively selected polypeptide fragments, for instance, a suitable heptapeptide can be combined with a suitable dipeptide, a suitable hexapeptide with a tripeptide, a suitable pentapeptide with a tetrapeptide. These various smaller peptide fragments can be used either in their unprotected or appropriately protected forms.

The following examples are presented to illustrate, but without limiting, the methods of carrying out the present invention, with the understanding that the protective groups used in the examples are only illustrative and not intended to restrict the compatible protective groups that can be used in carrying out the invention. Other compatible protective groups applicable in preparing the peptides of this invention, for example, to block a terminal amino group, include such groups as carbobenzyloxy-, tosyl-, phthalyl-, benzyl-, and para-substituted benzyl groups (as by $CH_3O$—, Br, etc), trityl-, formyl-, t-butyloxycarbonyl-, o-nitrophenylsulfenyl-, and t-amyloxycarbonyl-. Salt or ester formation such as methyl ester, ethyl ester, benzyl ester, t-butyl ester, or hydrazide formation can be used to block or protect the -COOH groups. Then O-acyl such as acetyl or benzoyl-, or O-alkyl-, or benzyl- can be used to protect the hydroxy group of threonine and serine. Nitro-, carbobenzyloxy-, adamantyloxy-, tosyl- and protonation can be used, for example, to protect the guanidine moiety of arginine; while such groups as acetamidomethyl-, benzyl- and p-methoxybenzyl- are useful to protect the sulfhydryl group of cysteine.

In the solid-phase synthesis of the peptides it is advantageous to select for use such protective groups that can be removed by hydrogen fluoride (HF) simultaneously with the liberation of the peptide from the carrier resin. In the synthesis of the peptides by solution methods the protective groups, depending on the synthetic approach, can be removed alternatively by acidic solvents such as HF or hydrogen bromide, by catalytic hydrogenation by using sodium in liquid ammonia, by Hg (II) or by alkaline hydrolysis.

The unprotected linear peptides, whether obtained by solid-phase or solution synthesis, are converted into their cyclized form by treatment with an oxidizing agent such as air, oxygen, potassium ferricyanide, or iodine, and carried out in a buffer at a pH ranging from 6.5 to 7.5 and beneficially at pH 7.2

EXAMPLE 1

Asp—Gln—Glu—Ser—Cys—Lys—Gly—Arg—Cys—Thr—Glu—Gly—Phe:
(with a bracket connecting the two Cys residues)

2.69 g. of tertiary-butyloxycarbonylphenylalanine (Boc-Phe) (10.2 mmol of Phe) are dissolved in 10 ml. of methanol and mixed with 96 ml. of 0.1N tetramethylammonium hydroxide in isopropanol/methanol (product of Merck A. G. of Darmstadt, West Germany, Catalog No. 8124).

The solution is evaporated under vacuum leaving an oily residue which is reevaporated twice from dioxane and finally from methanol. After drying under vacuum over $P_2O_5$, the residue (3.84 g.) is dissolved in 50 ml. of dimethylformamide (DMF) and stirred with 5.02 g. of the chloromethylated polypeptide-carrier polymer, Bio-Beads S-X1, 200 to 400 mesh (product of Bio-Rad Laboratories, 32nd and Griffin Ave., Richmond, Calif., having 1.1 mequ. (milliequivalent) of chlorine/g. of polymer), for 6 hours at room temperature. The polymer is filtered off and washed in sequence with 200ml. of DMF, 100 ml. of methanol, 100 ml. of water, and 100 ml. of methanol. The Boc-Phe-polymer product is dried under vacumm over $P_2O_5$ overnight and the weight of the dry Boc-Phe-polymer is 5.47 g. containing 0.39 millimoles of phenylalanine per g. of polymer.

Thereafter 2.58 g. of the Boc-Phe-polymer (equivalent to 1 mmol. of Boc-Phe) is placed in the reaction vessel of a Beckman Model 990 peptide synthetizer (designed for automatic synthesis of polypeptides by solid-phase technique, a product of Spinco Divison of Beckman Instruments, Inc., 1117 California Ave., Palo Alto, Calif. 94304, shown in their April 1972 descriptive bulletin 4SP64700) and the remaining 12 amino acid moieties or residues are built up on the Boc-Phe-polymer according to the following schedule:

1. washing 3 times with 25 ml. of chloroform for 1.5 mm.;
2. prewash with 25 ml. of trifluoroacetic acid-chloroform (TFA-CHCl₃) (1:3) for 1.5 min.;
3. deblocking with 25 ml. of (1:3) TFA-CHCl₃, 30 min.;
4. washing 3 times with 25 ml. of CHCl₃ for 1.5 min.;
5. prewash 2 times with 25 ml. of 10% (v/v) TEA-CHCl₃ (TEA is triethylamine) for 1.4 min.;
6. neutralization with 25 ml. of 10% (v/v) TEA-CHCl₃ for 10 min.;
7. washing 3 times wih 25 ml. of CHCl₃ for 1.5 min.;
8. washing 3 times with 25 ml. of methylene dichloride (CH₂Cl₂) for 1.5 min.;
9. introduction of 2.5 mmol. (2.5 equiv.) of the appropriate Boc-amino acid in 18 ml. of CH₂Cl₂ and mixing for 1.5 mm.;
10. addition of 2.5 mmol. of dicyclohexylcarbodiimide in 6 ml. of CH₂Cl₂ followed by a coupling time of 2 hours;
11. washing twice with 25 ml. of CH₂Cl₂, 1.5 min.;
12. washing twice with 25 ml. of ethanol, 1.5 min.;
13. washing twice with 25 ml. of CH₂Cl₂, 1.5 min; and
14. washing twice with 25 ml. of ethanol, 1.5 min.

Each Boc -amino acid was re-coupled in the following manner in order to improve yields:

15. washing 3 times with 25 ml. of CH₂Cl₂, 1.5 min.;
16. washing twice with 25 ml. of DMF-CH₂Cl₂ (1:1), 1.5 min.;
17. introducing 2.5 mmol. (2.5 equiv.) of the appropriate Boc-amino acid in 18 ml. DMF-CH₂Cl₂ (2:1) and mixing for 1.5 min.;
18. adding 2.5 mmol. of dicyclohexylcarbodiimide in 6 ml. of CH₂Cl₂ followed by a coupling time of 2 hours;
19. washing with 25 ml. of DMF-CH₂Cl₂ (1:1), 1.5 min.;
20. washing twice with 25 ml. of ethanol, 1.5 min.;
21. washing twice with 25 ml. of CH₂Cl₂, 1.5 min.;
22. washing twice with 25 ml. of ethanol, 1.5 min.

The cycle of steps 1 to 22 is repeated with each of the following blocked amino acids in sequence in building up the peptide chain: Boc-Gly, Boc-Glu (Bzl), Boc-Thr (Bzl), Boc-Cys(MeOBzl), Boc-Arg (Tos), Boc-Gly, Boc-Lys (Z), Boc-Cys (MeOBzl), Boc-Ser (Bzl), Boc-Glu (Bzl) Boc-Gln-ONp and Boc-Asp (Bzl).

The abbreviations of the amino acids, peptides and protecting groups follow the recommendations of the IUPAC-IUB Commission on Biochemical Nomenclature (*Biochemical Journal* 26, 773-780, 1972).

When the p-nitrophenyl ester of Boc-glutamine (Boc-Gln-ONp) is introduced in position 2 of the polypeptide, the following modification in schedule 1 is made:

In step 8 the washing solvent is DMF (12 ml.) instead of CH₂Cl₂ and in step 9 Boc-Gln-ONp (5.0 mmol) in DMF (9 ml.) is added, followed by a coupling time of 6 hours. In steps 10 and 11 the washing solvent is DMF (12 ml.). Then after step 14, steps 15 to 22 are carried out including again coupling the Boc-Gln-ONp residue in the same manner in step 17.

The dry weight of the solid fully protected tridecapeptide polymer adduct is 3.89 g.

The protected tridecapeptide polymer adduct (3.89 g.) then is treated with 50 ml. of HF for 1 hour at 0° C in the presence of 5 ml. of anisole. After removal of the HF and the anisole and drying, all under vacuum for 24 hours, the polymer is washed with ethyl acetate to remove any residual anisole. The crude product is suspended in a solution of 800 mg. of ammonium acetate in 8000 ml. of water and adjusted to pH 7.2 by addition of ammonia, which solution dissolves the tridecapeptide.

Half of this aqueous ammonium acetate solution of the tridecapeptide is evaporated under vacuum to about 1,000 ml. and then lyophilized, thereby also removing the ammonium acetate. The resulting tridecapeptide is its linear form (as of page 1, lines 8 to 10).

The other half of the foregoing aqueous ammonium acetate solution, after air oxidation for 6 days, is concentrated to 1,000 ml. by evaporation and then lyophilized thereby also removing the ammonium acetate. The residue crude cyclic tridecapeptide is refined by gel filtration on a SEPHADEX G-15 beads column using 0.2M AcOH as solvent. After rechromatography (3 times) on the same column a pure product is obtained. Yield 19% $(\alpha)_{D22} = -41.7°$ (C=1.0, 0.2M AcOH).

The SEPHADEX beads are a 3-dimensional network gel of epichlorhydrin cross-linked dextran chains having a high content of hydroxyl groups in its polysaccharide chains, whereby they are strongly hydrophilic and swell in water and aqueous electrolyte solution, and are a chromatographic material capable of separating substances according to molecular size. The SEPHADEX G-15 beads in the dry state have a diameter of 40 to 120 microns and retain peptides up to 1500 molecular weight (product of Pharmacia Fine Chemicals, of Uppsala, Sweden, and Piscatawny, N. J.).

Thin layer chromatography of the cyclic form of the tridecapeptide in isopropanol-1N AcOH (2:1, v/v), gives one single spot $R_f = 0.10$, positive to ninhydrin and chlorine-tolidine reagents. Amino acid analysis after hydrolysis in 6N HCl for 24 hours gives the following amino acid ratios (wherein the number within the parentheses are the theoretical values):

Asp 1.00 (1), Glu 3.00 (3), Ser 0.95 (1), Cys 2.28 (2), Lys 1.18 (1), Gly 2.14 (2), Arg 1.06 (1), Thr 1.00 (1), Phe 1.28 (1).

The linear form of the tridecapeptide can similarly be purified by chromatography on SEPHADEX G-15 using 0.2N HOAc as solvent in the presence of 1% mercapto-ethanol.

EXAMPLE 2

Asp—Gln—Glu—Lys—⌈Cys—Lys—Gly—Arg—Cys⌉—Thr—Glu—Gly—Phe.

1.56 g. of the Boc-Phe-polymer (0.60 mM of Phe) described in Example 1. is placed in the reaction vessel of the Beckman Model 990 peptide synthesizer and steps 1 – 22 described in Example 1, including the modifications for Boc - Gln - ONp, are carried out. The cycle of steps 1 – 22 is repeated for each of the following amino acids in order: Boc - Gly, Boc - Glu (Bzl), Boc - Thr (Bzl), Boc -Cys (MeOBzl), Boc - Arg (Tos), Boc - Gly, Boc -Lys (Z), Boc - Cys (MeOBzl), Boc - Lys (Z), Boc - Glu (Bzl), Boc - Gln - ONp, Boc - Asp (Bzl).

The dry weight of the fully protected tridecapeptide polymer adduct is 2.48 g.

The protected tridecapeptide polymer adduct is treated with HF containing 1% anisol and left at 0° C. for 45 min. After evaporation of the HF and extraction by ethyl acetate, the residue is dissolved in aqueous ammonium acetate solution (pH 7.2), saturated with air and the reaction mixture is left at room temperature for 5 days at a concentration of 100 mg. of the polypeptide per liter of buffer solution. Evaporation of the solvent and purification as described in Example 1, yields cyclic tridecapeptide Asp—Gln—Glu—Lys—⌈Cys—Lys—Gly—Arg—Cys⌉—Thr—Glu—Gly—Phe.

The obtained product is purified by gel chromatography on SEPHADEX G 15 (3 times) using 0.2 M AcOH as solvent, yielding 66 mg. pure peptide $(\alpha)_D^{22} = -43.7°$ (C = 1.0, 0.2 M HOAc). Electrophoresis (1200 V, 20 mA, 1 h.) at pH 5.0 in 0.05 M pyridine acetate buffer gives one single spot, positive to ninhydrin and chlorine-tolidine reagents ($R_f$ = 1.8 relative to phenylalanine). Amino acid analysis after hydrolysis in 6N HCl for 24 h. gives the following amino acid ratios (wherein the numbers within parentheses are the theoretical values):

Asp 0.9 (1), Glu 2.7 (3), Cys 2.2 (2), Lys 1.9 (2), Gly 1.9 (2), Arg 1.1 (1), Thr 1.1 (1), Phe 1.1 (1), NH₃ 1.0 (1).

EXAMPLE 3

Asp—Gln—Glu—Lys—⌈Cys—Lys—Gly—Arg—Cys⌉—OH.

10.13 g. of tertiary butyloxycarbonyl-S-p-methoxybenzyl-cysteine (Boc-Cys (MeOBzl) is attached on a chloromethylated carrier (27 g.) for peptides by the procedure described in Example 1. The weight of the dry Boc - Cys (MeOBzl) polymer was 33.08 g. containing 0.31 millimoles of cysteine per g. of polymer.

Thereafter 1.99 g. of Boc - Cys (MeOBzl)-polymer (equivalent to 0.62 mmol of Cys) is placed in the reaction vessel of a Beckman Model 990 peptide synthesizer and steps 1—22 as described in Example 1, including the modifications for Boc - Gln - ONp, are carried out. The cycle 1–22 is repeated for each of the following amino acids in order: Boc - Arg(Tos), Boc- Gly, Boc - Lys (Z), Boc - Cys (MeOBzl), Boc - Lys (Z), Boc - Glu (Bzl), Boc - Gln - ONp and Boc - Asp (Bzl).

The dry weight of the fully protected nonapeptide polymer adduct is 2.88 g.

The protected nonapeptide polymer adduct is treated with HF as described in Example 2. After the evaporation and washing procedures, the now unprotected nonapeptide is dissolved in a solution of ammonium acetate in water at pH 7.2 as described in Example 2. This ammonium acetate solution is air oxidized for 6 days. The work-up is performed as described in Example 1, and the product is purified by gel chromatography on SEPHADEX G-15 (3 times), using 0.2 M HOAc as solvent, yielding 92 mg. pure cyclic nonapeptide, $(\alpha)_D^{22} = -50.1°$ (C = 1.0, 0.2 M HOAc). Electrophoresis of the pure peptide on silica gel plates, at pH 4.7 in a buffer containing 2.5% acetic acid, 2.5 % pyridine, 5 % n-butanol and 90% water, at 1000 V, 50 mA gives one single spot positive to ninhydrin and chloridin-tolidine reagents ($R_f$ = 0.3 relative to lysine).

Amino acid analysis (figures within parentheses are the theoretical values):

Asp. 0.80 (1), Glu 1.85 (2), Lys 2.00 (2), Gly 1.10 (1), Arg 1.00 (1), Cys 2.20 (2). The growth promoting activity of the peptides of the invention is revealed and demonstrated by the data shown in table 1 for the tridecapeptide Asp—Gln—Glu—Ser—⌈Cys—Lys—Gly—Arg—Cys⌉—Thr—Glu—Gly—Phe.

These data show that the tridecapeptide increase the total number of cells produced. In this assay respectively different dosages of from 1 to 10 μug. of polypeptide per ml. of medium give a dose related increase, e.g. up to 10 μug. while higher dosages of the polypeptide seem to have a slight inhibitory effect.

TABLE 1.

| Calf Serum % | μg. tridecapeptide (cyclic) per ml. medium | No. of cells × 10⁶ | Growth stimulation in % |
|---|---|---|---|
| 0.67 | 0 | 2.05 | 0 |
| 0.67 | 1 | 2.35 | 14 |

TABLE 1.-continued

| Calf Serum % | μg. tridecapeptide (cyclic) per ml. medium | No. of cells × 10⁶ | Growth stimulation in % |
|---|---|---|---|
| 0.67 | 5 | 3.4 | 66 |
| 0.67 | 10 | 3.3 | 60 |
| 0.67 | 25 | 3.1 | 51 |
| 0.67 | 50 | 2.7 | 31 |

Tests of the growth promoting activity have been performed in human embryonic lung fibroblasts and the growth promoting activity is measured by cell counting in a counting chamber and expressed as per cent increase over a basal value obtained with using 0.67% calf serum.

The importance of this assay method is that it demonstrates that the whole cell cycle proceeds normally and is stimulated by the tridecapeptide, which is indicative of physiological as well as pharmacodynamic activity typical of compounds for use as drugs.

This invention also comprises treatment of the human body with the peptides (in each of their two forms) and pharnaceutical compositions in dose unit form comprising the compound.

The growth promoting activity of the peptides of the invention exemplified above, includes improving the in vitro cultivation of mammalian tissue cells in a tissue cell growth culture by incorporating into the tissue cell growth culture medium a such tissue cell growth enhancing effective amount (beneficially from about one to about ten micrograms per milliliter of the culture medium) of either form of the peptides of the invention.

The method of preparing the cyclic form of the peptides of the invention (as referred to above, and more fully illustrated by Example 2 above) involves preparing the cyclic form of peptides by oxidizing their linear form with a compatible oxidizing agent that, by its oxidizing effect, removes the hydrogen from the mercapto group of both of the cysteinyl moieties of the peptides, without adverse effect on any of the rest of the peptide, dissolved in an aqueous solvent medium for it (the peptide), such as aqueous ammonium acetate solution at a pH from about 6.5 to about 7.5 (e.g. adjusted by addition of ammonia for pH over 7). The oxidizing agent is used in an amount sufficient for accomplishing the removal of both of those hydrogens.

While the chloromethylated polypeptide-carrier polymer described in Example 1 is the so-called Merrifield beads (the chloromethylated copolymer of styrene with about one percent of divinylbenzene), corresponding beads can be used with the copolymer containing from one to two percent of the divinylbenzene or any other such peptide support or carrier or polypeptide fraction carrier can be used.

What is claimed is:

1. Synthetic peptides of the general formula

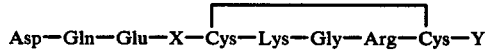

and the corresponding reduced, linear form where the link between the two Cys moieties in the oxidized form represents the dithio group, —S—S—; X = Ser or Lys; and Y = OH or Thr - Glu - Gly -Phe.

2. The linear tridecapeptide aspartyl-glutaminyl-glutamyl-seryl-cysteinyl-lysyl-glycly-arginyl-cysteinyl-threonyl-glutamyl-glycyl-phenylalanine.

3. The cyclic tridecapeptide:

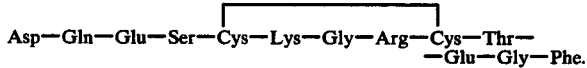

4. The linear tridecapeptide:

Asp - Gln - Glu - Lys - Cys - Lys -Gly - Arg - Cys - Thr - Glu - Gly - Phe.

5. The cyclic tridecapeptide:

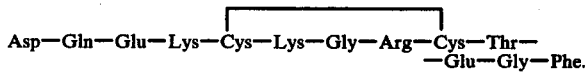

6. The linear nonapeptide:

Asp - Gln - Glu - Lys - Cys - Lys - Gly - Arg - Cys - OH.

7. the cyclic nonapeptide:

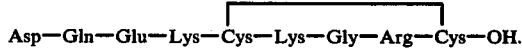

* * * * *

UNITED STATES PATENT AND TRADEMARK OFFICE
CERTIFICATE OF CORRECTION

PATENT NO. 4,058,512

DATED November 15, 1977

INVENTOR(S) Hans Sievertsson, Ronny Hugo Loritz Lundin and Gertrud Elisabeth Westin It is certified that error appears in the above-identified patent and that said Letters Patent are hereby corrected as shown below:

Column 1 line 32, the comma after "origin" should be a period; Column 1 line 50, "tein" should read -- teine --; column 1 line 57, the first occurrence of "acid" should read --acids,--; column 3 line 41, "mm." should read -- min. --; column 3 line 56, "mm." should read -- min. --;column 4 line 52, "page 1 lines 8 to 10" should read -- column 1 lines 20-21 --; column 4 line 61, "$(\alpha)_{D22=}-41.7$" should read -- $(\alpha)_D^{22} = -41.7$ --; column 5 line 42, "anisol" should read -- anisole --; column 6 line 8, "(MeOBzl)" should read -- (MeOBzl)) --; column 6 line 39, "$(\alpha)_D^{22}$" should read -- $(\alpha)_D^{22}$ --; column 6 line 57, "increase" should read -- increases --; column 6 lines 59 and 61, "uug." should read -- μg. --; and column 8 line 20, "glycly" should read -- glycyl --.

Signed and Sealed this

Seventeenth Day of July 1979

[SEAL]

Attest:

LUTRELLE F. PARKER

Attesting Officer    Acting Commissioner of Patents and Trademarks